United States Patent [19]

Dowrick et al.

[11] Patent Number: 4,472,374
[45] Date of Patent: Sep. 18, 1984

[54] VETERINARY COMPOSITIONS FOR REDUCING MAMMARY INFECTIONS

[75] Inventors: John S. Dowrick, Leigh; Peter Balderstone, Worthing, both of England

[73] Assignee: Beecham Group p.l.c., England

[21] Appl. No.: 423,448

[22] Filed: Sep. 24, 1982

[30] Foreign Application Priority Data

Sep. 25, 1981 [GB] United Kingdom ............... 8129093

[51] Int. Cl.³ ............................................ A61K 31/74
[52] U.S. Cl. ...................................... 424/78; 424/184; 424/358
[58] Field of Search ........................ 424/78, 184, 358

[56] References Cited

U.S. PATENT DOCUMENTS

| | | | |
|---|---|---|---|
| 3,239,414 | 3/1966 | Rowan | 424/184 |
| 3,697,653 | 10/1972 | Ongley | 424/184 |
| 4,012,497 | 3/1977 | Schopflin | 424/22 |
| 4,331,651 | 5/1982 | Reul et al. | 424/184 |

OTHER PUBLICATIONS

Alyushin et al.–Chem. Abst. vol. 82, (1975), pp. 47702p, 47703q.

*Primary Examiner*—Sam Rosen
*Attorney, Agent, or Firm*—Jacobs & Jacobs

[57] ABSTRACT

An intramammary composition containing a siloxane elastomer with incorporated antibacterial agent. The composition is of sufficiently low viscosity to facilitate application to the teat of a cow via the streak canal, and the composition remains sufficiently elastic to enable it to remain in place during the dry period and to allow it to be readily milked-out at the onset of lactation. The composition is useful in reducing mammary infections in cattle during their dry period and is compatible with conventional mastitis treatments at the end of lactation.

18 Claims, No Drawings

VETERINARY COMPOSITIONS FOR REDUCING MAMMARY INFECTIONS

This invention relates to veterinary compositions useful in a method of reducing mammary infections in cattle during their dry period.

During the lactating period mammary infections, such as mastitis in cattle, are conventionally treated by the intramammary infusion of an antibacterial agent in a suitable vehicle. Cattle are also vulnerable to such infection during their dry period, and for this reason are normally treated with an intramammary antibacterial preparation at the onset of their dry period. However, the efficacy of this dry period treatment inevitably diminishes during the course of the dry period with a consequent risk of infection, or re-infection. Thus, there is a need for an effective method of controlling mammary infections in cattle throughout the dry period.

In U.K. Pat. No. 1,441,747 one possible solution to this problem has been suggested. It is proposed in the Patent to inject the teats of cattle during their dry period, with a composition comprising an antibacterial agent, and a heavy metal salt in a solid or semi-solid base, which base melts at a temperature at or below the cattle body temperature. After administration, according to the Patent, the base melts sufficiently to allow the heavy metal salt to fall, under the action of gravity, to the bottom of the teat canal where it forms a physical plug which acts as a barrier to prevent re-infection of the teat canal. Apparently the antibacterial agent also acts to kill any bacterial infection already present.

It has now been found that certain silicon polymers can be used to achieve an effective seal in cattle teats, thereby reducing mammary infection of the treated cattle during their dry period. Antibacterial agents can be included in the silicon polymers to give a sustained release of the antibacterial agent into the teat and udder. There is no suggestion in U.K. Pat. No. 1,441,747 of the use of silicon polymers in this manner, nor of the advantageous results therewith.

Accordingly, the present invention provides a veterinary composition for reducing mammary infections in cattle during their dry period, which composition comprises a siloxane elastomer of sufficiently low viscosity to facilitate application to the teat by infusion, contained in an infusion means.

Furthermore, the present invention also provides a veterinary composition for reducing mammary infections in cattle during their dry period which composition comprises an antibacterial agent and a siloxane elastomer of sufficiently low viscosity to facilitate its application to the mammary gland by infusion.

By the term "siloxane elastomer", when used herein, is meant an elastomer comprising an elastic polymer of silicon containing repeating —Si—O— units. It will be realised that a siloxane elastomer for use according to the invention must be of sufficiently low viscosity to allow application to the teat by infusion and must remain sufficiently elastic during the period of use in order to retain the elastomer in place.

An antibacterial agent may be used in conjunction with the siloxane elastomer in order to further reduce mammarial bacterial infection during the 'dry period', or in order to control any existing bacterial infection and reduce the likelihood of re-infection.

Preferably, the antibacterial agent will be formulated with the siloxane elastomer. The antibacterial agent may be incorporated into the elastomer up to a level at which the necessary properties of the elastomer begin to break down. Normally we have found that a weight ratio of siloxane elastomer to incorporated antibacterial agent from 500 to 1 to 7 to 3 is satisfactory. Preferably the weight ratio of siloxane elastomer to incorporated antibacterial agent is 17 to 3 to 7 to 3.

Alternatively, the antibacterial agent or agents may be in the form of a solution, or a suspension. The suspension may comprise beadlets or granules containing an antibiotic in an aqueous-emulsifiable oil vehicle, as described in U.K. Patent Specification Nos. 1,312,918, 1,455,296 and 1,547,164. Preferably, the antibacterial suspension is in the form of a powdered antibacterial agent in a veterinarily acceptable oil vehicle. Two useful formulations containing a suspension of a penicillin in an oil vehicle are described in both European Patent No. 0 010 903 and in U.S. Pat. No. 4,282,202. Alternatively, a stable, aqueous suspension of a water insoluble salt of a penicillin G, such as described in U.S. Pat. Nos. 3,062,718, 2,793,153 and 2,897,120 may be used. The antibacterial solution or suspension may be infused into the mammary gland prior to injection of the siloxane elastomer.

The antibacterial agent may be any such agent that is effective in the treatment of mammarial bacterial infections and is compatible with the elastomer. Suitable examples of antibacterial agents include antibiotics such as neomycin, especially the sulphate, streptomycin, novobiocin, tetracycline, chlortetracycline, oxytetracycline and salts thereof; iodine, chlorine, or an agent(s) that releases these; phenolic compounds; quaternary ammonium salts; chlorhexidene; acridenes; penicillins such as ampicillin, ampicillin trihydrate, talampicillin, amoxycillin, nafcillin, carbenicillin, dicloxacillin, cloxacillin, benzathine cloxacillin, flucloxacillin, methicillin, ticarcillin, carefecillin; and mixtures of two pencillins such as ampicillin/flucloxacillin, amoxycillin/flucloxacillin, ticarcillin/flucloxacillin; and salts and hydrates thereof, such as ampicillin trihydrate/benzathine cloxacillin, bacterial agent will, of course, normally be incorporated into the elastomer at an antibacterially effective level. The antibacterial agent may be used in conjunction with a synergist. The penicillins, for example, may be used in combination with clavulanic acid.

As stated earlier in the specification the elastomer must also be of sufficiently low viscosity to facilitate application to the mammary gland by injection. Thus within this criterion many siloxane polymers are suitable for use in this invention and the skilled reader will readily be able to formulate satisfactory elastomers from readily available silicon polymers using his skill and technical knowledge.

We have found that suitable siloxane elastomers contain repeating

units, wherein R is a hydrocarbon group containing one to six carbon atoms. Suitable examples of the group R include $C_{1-6}$ alkyl such as methyl, ethyl and propyl; $C_{1-6}$ alkenyl such as vinyl; and phenyl. Preferably R is a $C_{1-4}$ alkyl group such as methyl.

Such elastomers can be prepared by the curing of silicon polymers of smaller chain length and/or less cross-linked structure in the usual way. In order to ensure that the resultant elastomer is of sufficiently low viscosity for use in this invention an inert fluid silicone can be included in the un-cured material, if necessary. For example, a liquid elastomer of the desired properties can be obtained by curing a polymer which would normally yield a solid rubber in the presence of an inert silicone fluid.

A particularly suitable siloxane elastomer for use according to the invention can be prepared by the curing of Silastic 382, a two component room temperature vulcanising silicon polymer (manufactured by Dow Corning) in the presence of silicone fluid. One component of Silastic 382 is a polydimethyl siloxane of fairly short chain length, which chains are terminated by hydroxyl groups, and a propylorthosilicate cross-linking agent. The curing process is a catalytically induced condensation reaction between these terminal hydroxyl groups and the cross-linking agent. Suitable catalysts include stannous octoate, which is the second component of Silastic 382. In the absence of a silicone fluid the cured product is a solid rubber. Accordingly, sufficient silicone fluid is added to the un-cured Silastic 382 to ensure that the cured product is an elastomer with the necessary properties. In the particular case of Silastic 382 a mixture of approximately 16% Silastic 382 in Silicone Fluid F111/500 (manufactured by I.C.I.) gives a very suitable siloxane elastomer on curing which elastomer is mildly adhesive and is soft enough for ready milk-out at the end of the dry period.

From the aforesaid it can be seen that one preferred method of the invention comprises infusing the teats of the cattle with a veterinary composition which composition comprises 0.2 to 30% of an antibacterial agent incorporated in a siloxane elastomer. Such compositions are believed to be novel and as such represent an important aspect of the invention.

It has been found that to obtain the best results the majority of the elastomer (optionally together with an antibacterial agent) is infused into the teat sinus, and the rest of the elastomer is discharged into the streak canal while the infusion means is withdrawn out of the teat. The result is an efficient seal with the lower portion of the teat sinus and the streak canal filled with elastomer.

Siloxane elastomers for use in the veterinary compositions according to the invention have been found to provide an effective teat seal which reduces mammary infections in cattle during their dry period. Further, elastomers containing antibacterial agents give a sustained release of the agents into the teat and udder which treats any residual infection present at the time of injection and reinforces the sealing effect obtained with the elastomer by maintaining bacteriocidal levels of the active ingredient. The elastomers are sufficiently soft to be milked-out at the onset of lactation. It has generally been found that a single application of the elastomer is all that is needed to provide adequate protection throughout the dry period.

The elastomers can conveniently be administered to the teat by syringe through either a plastic cannula or a wide-bore needle, or by a non-cannula means. However, any infusion means suitable for intramammary administration can be used, or readily adapted for such use. A suitable infusion means is a syringe known as a 'mastitis applicator'.

In the case of an elastomer used in conjunction with an antibacterial solution or suspension, the combination may be infused into the teat using a number of devices. The combination may be infused simultaneously using a normal one cylinder syringe, fitted with a suitable needle, such that the antibacterial solution or suspension enters the teat first, followed by the elastomer. The antibacterial solution or suspension may be infused using a separate syringe to that used to infuse the elastomer. Alternatively, two linked syringes, each containing either the antibacterial solution or suspension, or the elastomer, and feeding into one needle may be used.

The invention further provides a method of reducing mammary infection in cattle during their dry period which method comprises infusing the teats of the cattle with a siloxane elastomer.

A convenient volume of elastomer for the treatment of a single teat is 0.1 to 5 ml., suitably 0.2 to 1.0 ml.

The compositions of the invention should be applied at the end of lactation.

The following Examples illustrate the invention:

EXAMPLE 1

A siloxane elastomer was prepared in the following manner.

24.0 g of Silastic 382+ was mixed with 126.0 g of Silicone Fluid F111/500++ using a paddle stirrer. When a homogeneous mixture was obtained 0.25 ml of the curing catalyst was added into the mixture with continuous stirring.

The resultant siloxane elastomer was filled into a batch of 0.5 ml syringes. Using these syringes 0.3 ml of elastomer was infused into the teats of a cow, 0.2 ml into the teat sinus, the remaining 0.1 ml during withdrawal through the streak canal.

EXAMPLE 2

A siloxane elastomer container benzathine cloxacillin and ampicillin trihydrate was prepared using the following formulation:

| | |
|---|---|
| Silastic 382+ | 9.5 g |
| (Catalyst+ | 6 drops) |
| Silicone Fluid 200+++ | 30.5 g |
| (200 centistokes) | |
| Silicone Fluid 200+++ | 35.0 g |
| (30,000 centistokes) | |
| Ampicillin Trihydrate | 7.5 g |
| Benzathine Cloxacillin | 17.5 g |

+Silastic 382 is a two component room temperature vulcanising silicone elastomer manufactured by Dow Corning. The first component is a polydimethyl siloxane and a propylorthosilicate cross-linking agent. The second component is a stannous octoate curing catalyst.
++Silicone Fluid F111/500 is manufactured by I.C.I. and is a silicone fluid having a viscosity of 500 centistokes.
+++Silicone Fluid 200 is manufactured by Dow Corning, and is a silicone fluid.

The antibiotics were mixed to a fine paste with the silicone fluids using a motorised pestle and mortar mill. The silastic elastomer was added and fully mixed in. The catalyst was then mixed in. Finally, the composition was packaged into a number of syringes which were sealed and sterilised by exposure to gamma irradiation.

We claim:

1. A veterinary composition for reducing mammary infections in cattle during their dry period, which composition comprises a catalytically cross-linked siloxane elastomer of sufficiently low viscosity to facilitate application to the mammary gland by injection, contained in an injection means.

2. A veterinary composition as claimed in claim 1 which also comprises an antibacterial agent.

3. A veterinary composition as claimed in claim 2, wherein the antibacterial agent is incorporated into the siloxane elastomer, the weight ratio of siloxane elastomer to antibacterial agent being 500 to 1 to 7 to 3.

4. A veterinary composition as claimed in claim 3, wherein the ratio of siloxane elastomer to incorporated antibacterial agent by weight is 17 to 3 to 7 to 3.

5. A veterinary composition as claimed in claim 2, in which the composition also comprises an antibacterial agent in the form of a solution or suspension.

6. A veterinary composition as claimed in claim 2 wherein the antibacterial agent comprises ampicillin trihydrate or benzathine cloxacillin or mixtures thereof.

7. A veterinary composition as claimed in claim 1, wherein the siloxane elastomer comprises an elastic polymer of silicon containing repeating units of a formula:

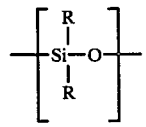

wherein R is a $C_{1-6}$ alkyl, $C_{1-6}$ alkenyl or a phenyl group.

8. A veterinary composition as claimed in claim 1, in dosage unit form, suitable for the treatment of a single teat.

9. A veterinary composition as claimed in claim 8, wherein the dosage unit comprises 0.1 to 5 ml, of siloxane elastomer.

10. A method of reducing mammary infections in cattle during their dry period which comprises injecting the teats of cattle with a veterinary composition as claimed in claim 2, in an amount sufficient to seal said teats with said elastomer.

11. A veterinary composition for reducing mammary infections in cattle during their dry period, which composition comprises an antibacterial agent, and a catalytically cross-linked siloxane elastomer of sufficiently low viscosity to facilitate its application to the mammary gland by injection.

12. A method of reducing infections in cattle during the dry period, which comprises infusing via an infusion means into the teat sinus of a teat of said cattle a first portion of a veterinary composition comprising a catalytically cross-linked siloxane elastomer of sufficiently low viscosity to facilitate such infusion and filling the streak canal of said teat with said elastomer, whereby said teat is sealed, by infusing a second portion of said veterinary composition into the streak canal of said teat while said infusion means is withdrawn out of said teat, said second portion being effective to fill said streak canal with said elastomer.

13. The method according to claim 12, wherein said veterinary composition also comprises an antibacterial agent.

14. The method according to claim 13, wherein the antibacterial agent is incorporated into the siloxane elastomer, the weight ratio of siloxane elastomer to antibacterial agent being 500 to 1 to 7 to 3.

15. The method according to claim 13, wherein the antibacterial agent comprises ampicillin trihydrate or benzathine cloxacillin or mixtures thereof.

16. The method according to claim 15, wherein the siloxane elastomer comprises an elastic polymer of silicon containing repeating units of a formula:

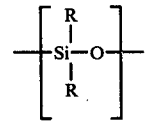

wherein R is a $C_{1-6}$ alkyl, $C_{1-6}$ alkenyl or a phenyl group.

17. The method according to claim 12, wherein the majority of said veterinary composition is infused into said teat sinus and the remainder thereof is infused into said streak canal.

18. The method according to claim 13, wherein the majority of said veterinary composition is infused into said teat sinus and the remainder thereof is infused into said streak canal.

* * * * *